United States Patent
Buss et al.

(10) Patent No.: US 8,546,601 B2
(45) Date of Patent: Oct. 1, 2013

(54) STORAGE-STABLE 2-HYDROXY-4-(METHYLTHIO)BUTYRONITRILE

(75) Inventors: Dieter Buss, Wesseling (DE); Martin Steurenthaler, Frankfurt (DE); Joachim Hans Hasselbach, Gelnhausen (DE); Michael R. Rinner, Singapore (SG); Benjamin Fonfe, Frankfurt (DE); Martin Koerfer, Kahl (DE); Stephan Kretz, Biebergemuend (DE)

(73) Assignee: Evonik Degussa GmbH, Essen (DE)

( * ) Notice: Subject to any disclaimer, the term of this patent is extended or adjusted under 35 U.S.C. 154(b) by 32 days.

(21) Appl. No.: 13/402,032

(22) Filed: Feb. 22, 2012

(65) Prior Publication Data

US 2012/0215021 A1   Aug. 23, 2012

Related U.S. Application Data

(60) Provisional application No. 61/445,746, filed on Feb. 23, 2011.

(51) Int. Cl.
*C07C 319/20* (2006.01)
*C07C 323/12* (2006.01)
*C07C 323/58* (2006.01)

(52) U.S. Cl.
USPC ............ 558/315; 558/438; 562/559; 562/581

(58) Field of Classification Search
None
See application file for complete search history.

(56) References Cited

U.S. PATENT DOCUMENTS

| 2,745,745 | A | 5/1956 | Blake et al. |
| 4,912,257 | A | 3/1990 | Hernandez et al. |
| 4,960,932 | A | 10/1990 | Gillonnier et al. |
| 5,756,803 | A | 5/1998 | Casse et al. |
| 2006/0030739 | A1 | 2/2006 | Dubner et al. |

FOREIGN PATENT DOCUMENTS

| EP | 0330527 | 8/1989 |
| JP | 2002-105048 A | 4/2002 |
| WO | WO 96/40631 | 12/1996 |
| WO | WO2006/015684 | 2/2006 |

*Primary Examiner* — Kamal Saeed
(74) *Attorney, Agent, or Firm* — Oblon, Spivak, McClelland, Maier & Neustadt, L.L.P.

(57) ABSTRACT

A storage stable mixture containing 86 to 97% by weight of 2-hydroxy-4-methylthiobutyronitrile, 2 to 14% by weight of water, 0.05 to 0.5% by weight of HCN and having a pH of 1 to 4, measured using a pH electrode at 23° C. is provided. A method to produce the storage stable mixture and its use in manufacture of DL-methionine or 2-hydroxy-4-methylthiobutyric acid is also provided.

22 Claims, 1 Drawing Sheet

STORAGE-STABLE 2-HYDROXY-4-(METHYLTHIO)BUTYRONITRILE

CROSS REFERENCE TO RELATED APPLICATIONS

This application claims priority to U.S. Provisional Application No. 61/445,746, filed Feb. 23, 2011, the disclosure of which is incorporated herein by reference in its entirety.

BACKGROUND OF THE INVENTION

The invention relates to a 2-hydroxy-4-(methylthio)butyronitrile (MMP-CN) mixture having very good storage stability which may be produced from 3-(methylthio)propanal (methylmercaptopropionaldehyde, MMP) and hydrogen cyanide (HCN) and also the method for production thereof. In particular, the invention describes a process for synthesizing storage-stable MMP-CN aqueous mixture, which contains superstoichiometric amounts of prussic acid, in relation to the unreacted MMP.

2-Hydroxy-4-(methylthio)butanenitrile (MMP-cyanohydrin) is an intermediate for the synthesis of D,L-methionine and the methionine hydroxyl analog 2-hydroxy-4-methylthiobutyric acid (MHA). Methionine is an essential amino acid which is used, inter alia, as supplement in feedstuffs. MHA is a liquid methionine substitute having low bioavailability.

From MMP, by reaction with hydrogen cyanide (prussic acid), MMP-cyanohydrin (2-hydroxy-4-(methylthio)butyronitrile) may be produced using suitable catalysts. Suitable catalysts are, e.g., pyridine or triethylamine. By hydrolysis of MMP-cyanohydrin with, e.g., mineral acids, MHA is obtained. Methionine is formed by reaction of MMP-cyanohydrin with ammonium hydrogencarbonate, with formation of hydantoin, which can be saponified with a base, e.g. potassium carbonate or sodium hydroxide. Methionine is liberated with carbon dioxide or sulfuric acid.

It is known, for example, from U.S. Pat. No. 4,960,932, to produce methionine by a four-stage method. In the first step, by addition of HCN to MMP in the presence of triethylamine, the MMP-cyanohydrin is produced. The amount of HCN used corresponds to 1.05 mol in relation to the amount of MMP used. Then, the MMP-cyanohydrin, in a second step, is reacted with ammonia, whereby 2-amino-4-methylthiobutyronitrile is formed which, in a third step, is then hydrolyzed in the presence of a ketone and an alkali metal hydroxide, forming methylthiobutyramide which is finally saponified to form an alkali metal methioninate.

In the case of production of 2-hydroxy-4-methylthiobutyric acid (MHA), the 2-hydroxy-4-methylthiobutyronitrile is obtained by reacting MMP and HCN in a medium that contains pyridine or an amine (see U.S. Pat. No. 2,745,745, column 2, lines 52 to 55). Excess HCN is merely distilled off, e.g. in a vacuum. The resultant 2-hydroxy-4-methylthiobutyronitrile is then hydrolyzed with sulfuric acid, whereby the amide of 2-hydroxy-4-methylthiobutyric acid is directly formed, and finally 2-hydroxy-4-methylthiobutyric acid is formed. A similar method is also described in EP A 330 527 A1 or in U.S. Pat. No. 4,912,257.

In addition, in WO 96/40631 A1, the production of MMP-cyanohydrin by reacting MMP with hydrogen cyanide in the presence of a suitable addition reaction catalyst is described. According to this reference, triisopropanolamine, nicotinamide, imidazole, benzimidazole, 2-fluoropyridine, poly-4-vinylpyridine, 4-dimethylaminopyridine, picoline or pyrazine can serve as addition reaction catalysts for producing MMP-cyanohydrin. Furthermore, trialkylamines having three to eighteen carbon atoms in each of the alkyl substituents bound to the nitrogen atom and tertiary amines in which at least one of the non-hydrogen substituents bound to the nitrogen atom contains an aryl group can also serve for catalyzing the reaction between MMP and hydrogen cyanide to form MMP-cyanohydrin.

Preferably, in this case, the hydrogen cyanide is used in a molar excess of about 2%, based on MMP.

WO 2006/015684 A2 finally discloses a method for, in particular, continuous production of MMP or of MMP-cyanohydrin in which in each case heterogeneous amine catalysts are used for the addition reaction.

In addition, it is known from U.S. Pat. No. 5,756,803 to react an aldehyde with hydrogen cyanide in the presence of a buffer, by means of which the pH of the solution can be set above 4, amines being excluded. Quite generally, as buffer, mixtures of alkali metal salts of acids and acids, or mixtures of acids and alkali metal hydroxides can be used. The buffer is used in order firstly to avoid the decomposition of the starting materials and of the desired product and secondly to neutralize the acids used for stabilizing hydrogen cyanide. Likewise, here, HCN is added in a molar excess to the MMP, the molar excess preferably being in the range from 2 to 5%. In the reaction of MMP with HCN in the presence of the conventional bases, although the bases increase the reaction rate under the conditions specified, they rapidly lead to a decomposition of the cyanohydrin formed and to decomposition of the aldehyde used at the start, forming a highly discolored solution. Therefore, the use of a buffer system likewise has a beneficial effect on product stability.

In order to recover the residual amounts of unreacted HCN and MMP contained in the exhaust gas of the reactive absorber, and for avoiding the problem of formation of byproducts, U.S. Pat. No. 5,756,803 provides a water scrubber which is connected downstream, with large amounts of scrubbing water passing into the product which firstly, for production of methionine, need to be at least partially removed and which secondly again promote the decomposition of the MMP-cyanohydrin which in each case is a not inconsiderable disadvantage. The water content in the product is approximately 48% by weight.

Therefore, the product described in U.S. Pat. No. 5,756,803 is also not storage stable and, for storage and in particular for transport, must be processed in a complex manner by means of removal of the water by distillation, which is a great economic disadvantage of the method.

JP2002-105048 finally discloses a method for producing storage-stable 2-hydroxy-4-(methylthio)butanenitrile. In this case the 2-hydroxy-4-(methylthio)butanenitrile is produced from MMP by reaction with hydrogen cyanide (prussic acid) using suitable catalysts. Suitable catalysts are, e.g., pyridine, triethylamine or an inorganic base such as potassium carbonate or ammonia. The amount of hydrogen cyanide used is 1 to 1.1, preferably 1.02 to 1.08 per mole of MMP. The reaction proceeds at 5° C. to 40° C. at residence times between 0.5 and 3 hours. For stabilizing the hydrogen cyanide, 30 to 80 parts by weight (23 to 44% by weight) of water, based on the amount used of 100 parts by weight of MMP are added to the mixture. For further product stabilization, an acid is also added to the product after any downstream workup step, the pH being set to between 1 and 6, or preferably between 1 and 5.

Likewise, JP2002-105048, for the enhanced stability of hydrogen cyanide, describes the addition of water in the reaction, preferably up to a content of 23 to 44% by weight, based on MMP used, which leads to the same disadvantages.

For the MMP-cyanohydrin provided in JP2002-105048, a storage stability, merely on the basis of color values, was also shown for a period of only 11 days (264 h). A long-term stability in the range of several weeks was not shown and is also not achieved using a product according to JP2002-105048, as the inventors have discovered. However, a long-term stability in the range of several weeks is especially desirable because only in this manner can long-term safe and loss-free storage be achieved, and the product can only then, even after several weeks of intermediate storage or transport time advantageously be used in the production of the above-mentioned valuable materials methionine or MHA.

The substantial disadvantages of the MMP-cyanohydrin products previously described in the literature and of the associated production methods are that the products are sufficiently storage stable for only a relatively short time, that is to say in the range of some days, or the methods provide products that are only stable for a short time.

It is a further disadvantage that for achieving a high MMP-CN yield in the production method, previously high molar excesses of HCN have to be used. The excess amounts of HCN are lost in the methods described and are a great economic disadvantage.

Furthermore, the catalysts used in the methods described also promote the formation of unwanted byproducts from the aldehydes used, which lead to contamination of the product which cannot be tolerated.

SUMMARY OF THE INVENTION

It was an object of this invention to prepare a cyanohydrin that is storage stable for a relatively long time, in particular at least 4 weeks, preferably MMP-cyanohydrin, and to provide a method which catalyzes the reaction of aldehydes, in particular of MMP with hydrogen cyanide. The method should at the same time show marked improvements with regard to yields with respect to the aldehyde and hydrogen cyanide used. In particular, the method should provide a product having a very low molar residual MMP content. Furthermore, the method, in contrast to the methods described in the literature, should succeed as far as possible without further addition of water.

These and further objects are achieved by the present invention, the first embodiment of which provides a 2-hydroxy-4-methylthiobutyronitrile mixture, comprising:

86 to 97% by weight of 2-hydroxy-4-methylthiobutyronitrile;

2 to 14% by weight of water; and 0.05 to 0.5% by weight of HCN; wherein a pH of the 2-hydroxy-4-methylthiobutyronitrile mixture is from 1 to 4, measured with a pH electrode at 23° C.

In a preferred embodiment the 2-hydroxy-4-methylthiobutyronitrile mixture is storage stable having a loss of 2-hydroxy-4-methylthiobutyronitrile in the mixture on storage for 128 days of less than 1% by weight.

In a second embodiment the present invention provides a method for producing the 2-hydroxy-4-(methylthio)butyronitrile mixture, comprising:

a) reacting 3-methylmercaptopropionaldehyde with hydrogen cyanide in the presence of a base to form a reaction mixture comprising the 2-hydroxy-4-methylthiobutyronitrile;

b) adjusting the water content of the reaction mixture to 2 to 14% by weight by water addition, optionally during the reaction, after the reaction or during and after the reaction;

c) adjusting the HCN content of the reaction mixture to 0.05 to 0.5% by weight by HCN addition, optionally during the reaction, after the reaction or during and after the reaction; and thereafter, d) adding acid to set the pH to 1-4.

In a further preferred embodiment of this method the molar ratio of hydrogen cyanide to 3-methylmercaptopropionaldehyde is from 0.98 to 1.03.

In a third embodiment, the present invention provides method for producing the 2-hydroxy-4-(methylthio)butyronitrile mixture, comprising:

a) preparing a mixture of 3-methylmercaptopropionaldehyde and a base having a water content of 2 to 14% by weight;

b) adjusting the pH of the mixture to 4.5 to 6.0;

c) adding HCN to the mixture having a pH of 4.5 to 6.0;

d) reacting the 3-methylmercaptopropionaldehyde with the HCN in the presence of the base at a temperature of from 20 to 80° C. to form a reaction mixture comprising the 2-hydroxy-4-methylthiobutyronitrile;

e) adjusting the HCN content of the reaction mixture to 0.05 to 0.5% by weight by HCN addition; and thereafter, f) adding acid to set the pH to 1-4, wherein pH adjustment is with a pH electrode at 23° C., and wherein a molar ratio of hydrogen cyanide to 3-methylmercaptopropionaldehyde in d) is from 0.98 to 1.03.

DETAILED DESCRIPTION OF THE PREFERRED EMBODIMENTS

The present invention provides a 2-hydroxy-4-methylthiobutyronitrile mixture, comprising:

86 to 97% by weight of 2-hydroxy-4-methylthiobutyronitrile;

2 to 14% by weight of water; and 0.05 to 0.5% by weight of HCN; wherein a pH of the 2-hydroxy-4-methylthiobutyronitrile mixture is from 1 to 4, measured with a pH electrode at 23° C.

The storage stability of the mixture containing 2-hydroxy-4-ethylthiobutyronitrile having the HCN and water contents and pH range according to the invention may be particularly high, as examples 3a, 3c, 5a and 5b show. The setting of the pH to a preferred range of 2-3 may additionally increase the storage stability of the product mixture (examples 3a and 5a).

In a preferred embodiment of the present invention, storage stabilities of at least 128 days may be achieved in which less than 1% loss of 2-hydroxy-4-methylthiobutyronitrile, in particular from 0.01 to 0.73% losses, are observable. Such stability represents a marked improvement in comparison with conventionally obtained 2-hydroxy-4-methylthiobutyronitrile mixtures as described above, and as shown by comparative example 5c not according to the invention with a 2-hydroxy-4-methylthiobutyronitrile-containing mixture having 0.01% by weight of HCN and 18.12% by weight of water at pH 4 shows, in which 3.28% loss of 2-hydroxy-4-methylthiobutyronitrile occurred. Likewise, in comparative example 4b not according to the invention, a mixture containing 2-hydroxy-4-methylthiobutyronitrile with 0.04% by weight of HCN and 17.23% by weight of water, 1.70% loss of 2-hydroxy-4-methylthiobutyronitrile occurred.

Therefore, in a further preferred embodiment of the present invention a storage stable mixture comprises 88 to 92% by weight of 2-hydroxy-4-methylthiobutyronitrile, 3 to 12% by weight of water and/or 0.1 to 0.3% by weight of HCN and/or has a pH of 2 to 3.

The mixture containing 2-hydroxy-4-(methylthio)butyronitrile is preferably produced according to the invention by a method, comprising:

a) reacting 3-methylmercaptopropionaldehyde with hydrogen cyanide in the presence of a base to form a reaction mixture comprising the 2-hydroxy-4-methylthiobutyronitrile;

b) adjusting the water content of the reaction mixture to 2 to 14% by weight by water addition, optionally during the reaction, after the reaction or during and after the reaction;

c) adjusting the HCN content of the reaction mixture to 0.05 to 0.5% by weight by HCN addition, optionally during the reaction, after the reaction or during and after the reaction; and thereafter d) adding acid to set the pH to 1-4.

In the reaction the temperature may be from 20 to 80° C. and a molar ratio of hydrogen cyanide to 3-methylmercaptopropionaldehyde is from 0.98 to 1.03, preferably 0.99 to 1.01.

It is possible here already during the reaction of MMP with HCN to obtain the desired water content or HCN content by means of water already present in the starting materials or the appropriately supplied amount of HCN.

Thus in another embodiment of the present invention, the method comprises:

a) preparing a mixture of 3-methylmercaptopropionaldehyde and a base having a water content of 2 to 14% by weight;

b) adjusting the pH of the mixture to 4.5 to 6.0;

c) adding HCN to the mixture having a pH of 4.5 to 6.0;

d) reacting the 3-methylmercaptopropionaldehyde with the HCN in the presence of the base at a temperature of from 20 to 80° C. to form a reaction mixture comprising the 2-hydroxy-4-methylthiobutyronitrile;

e) adjusting the HCN content of the reaction mixture to 0.05 to 0.5% by weight by HCN addition; and thereafter, f) adding acid to set the pH to 1-4, wherein pH adjustment is with a pH electrode at 23° C., wherein a molar ratio of hydrogen cyanide to 3-methylmercaptopropionaldehyde in d) is from 0.98 to 1.03.

A mixture containing 2-hydroxy-4-(methylthio)butyronitrile prepared in either manner may have the described storage stability and therefore, may be particularly suitabile as feedstock for the production method for methionine. The latter has its cause, in particular, in the favorable molar HCN/MMP ratio of ≥1.

In an especially preferred embodiment of the production method according to the present invention, 3-methylmercaptopropionaldehyde may be reacted with hydrogen cyanide in the presence of a base as catalyst in a main reaction zone of a reactor to form the nitrile. Residual amounts of gaseous hydrogen cyanide (HCN), which leave the main reaction zone are absorbed in an absorption and post-reaction zone of the reactor which contains a mixture of 3-methylmercaptopropionaldehyde and catalyst and optionally 2-hydroxy-4-(methylthio)butyronitrile. At least a part of the residual HCN reacts with the 3-methylmercapto-propionaldehyde in the post reaction zone to form additional 2-hydroxy-4-(methylthio)butyronitrile. Preferably most of the residual HCN reacts with the 3-methylmercapto-propionaldehyde in the post reaction zone and most preferably, to maximize yield, all the residual HCN reacts with the 3-methylmercapto-propionaldehyde in the post reaction zone to form additional 2-hydroxy-4-(methylthio)butyronitrile.

Particular preference may also be given to the mixtures containing 2-hydroxy-4-(methylthio)butyronitrile that are produced by the preferred method according to the invention, since these mixtures have a particularly good storage stability as examples 3a) and 3c) according to the invention show.

In this manner, storage stabilities of at least 128 days are achieved in which a loss of 2-hydroxy-4-methylthiobutyronitrile of a maximum of only 0.01 to 0.64% may be observed. Production of the mixture according to the invention using the preferred method cited therefore completely surprisingly may achieve a great improvement in storage stability.

The residual content of HCN in the gas phase reacts, in the preferred embodiment, owing to the absorption or condensation predominantly with the aldehyde to form the cyanohydrin. Owing to the effective removal of the HCN from the gas phase, it may be possible, in contrast to the conventionally known methods to use a molar ratio of hydrogen cyanide to aldehyde of 0.99 to 1.01, which may provide a great economic advantage according to the methods of the present invention.

The invention also relates, in particular, to a method for the addition reaction of hydrogen cyanide to MMP in the presence of a base, in particular an amine, wherein the method may be arranged in such a manner that residual contents of gaseous hydrogen cyanide are absorbed outside a main reaction zone at temperatures of about 0° C. to 25° C. into a liquid mixture of the aldehyde MMP and the reaction product from MMP with hydrogen cyanide and catalyst and then further reacted with MMP.

By means of the method according to the invention, in general, aldehydes containing 1 to 6 carbon atoms which if desired are substituted with alkyl, alkoxy or alkylthio, may be advantageously reacted with hydrogen cyanide.

In a preferred embodiment according to the present invention, the mixture contained in the absorption and post-reaction zone originates at least partially from the main reaction zone. A dilution with foreign materials or foreign solvents may thereby be prevented, in contrast to U.S. Pat. No. 5,756,803.

The main reaction zone may comprise either a stirred reactor or a loop reactor. Both embodiments lead to a rapid and good mixture and a rapid conversion of MMP and HCN.

The main reaction zone may also additionally contain a jet pump. This may lead to a further intensification of mixing of the reaction components and may be used concomitantly particularly advantageously for drawing HCN into the main reaction zone.

The post reaction may proceed as stated above between an HCN-containing gas and a liquid. It then takes place in an absorption and post-reaction zone which preferably contains a device for contacting a gas with a liquid, in particular a column such as, for example, a tray column, a packed-bed column, a bubble-column reactor, a droplet column or optionally a reactor having a mechanically agitated container, or a submerged jet reactor.

The absorption zone and the post-reaction zone may also be part of a loop reactor, which effects high mixing and rapid reaction of the components.

In the method according to the invention, substantially gaseous hydrogen cyanide may be introduced into the main reaction zone, preferably a hydrogen-cyanide-containing product gas from a hydrogen cyanide production process which is connected to the reactor.

The hydrogen cyanide content of the gas mixture used ranges from 1 to 99% by weight, preferably from 5 to 75% by weight, particularly preferably 6-22% by weight. The hydrogen cyanide may be produced, in particular, by the Andrussow method as per DE 102007034715A1 or else by what is termed the BMA method in German ("Blausäure aus Methan and Ammonik" [prussic acid from methane and ammonia]) as per DE 1041476 (reactor). Both methods are also described in Ullmann's Encyclopedia of Industrial Chemistry, 1987 VCH-Verlagsgesellschaft mbH, chapter "Cyano Compounds Inorganic", section 1.2.1-1.2.2. The ammonia present is removed in each case from the product gas. The product gas from the Andrussow method (Andrussow gas) contains, after the removal of ammonia, typically about 10% by weight of hydrogen cyanide, in contrast, the product gas from the BMA method (BMA gas) contains about 70% by weight of hydrogen cyanide.

Thus, the typical product gas compositions of the Andrussow method have approximately the following contents: 10.3% by weight of HCN, 3.7% by weight of $H_2O$, 1.3% by weight of $H_2$, 75.8% by weight of $N_2$, 0.4% by weight of $O_2$, 6.3% by weight of CO, 0.6% by weight of $CO_2$, 0.4% by weight of $CH_4$, 1.3% by weight of Ar, those of the BMA method about 68.3% by weight of HCN, 6.7% by weight of $H_2O$, 17.3% by weight of $H_2$, 3.6% by weight of $N_2$, 4% by weight of $CH_4$.

The direct use of the product gas has the considerable advantage that no upstream and energy-intensive liquefaction of the hydrogen cyanide need proceed and with corresponding coupling to a plant for producing hydrogen cyanide gas, considerable capital costs in corresponding process steps for the absorption and distillation of HCN may be saved. The further gas fractions in addition to HCN surprisingly do not have a disadvantageous effect on the cyanohydrin yield.

The residual gas of the MMP-cyanohydrin production and hydrogen cyanide production may then be utilized jointly or burnt. In the latter case, the resultant energy may be reused for operating both methods, which means more degrees of freedom and a considerable economic advantage.

A preferred embodiment of the method according to the invention and a corresponding device are outlined in FIG. 1, which is described in more detail hereinafter:

When a tray column or a packed-bed column is used for the reactive absorption, the gas flow which contains the prussic acid is fed into the bottom phase (A) of the column (C) or preferably already contacted with the aldehyde solution via a gas blower (B), which aldehyde solution is circulated (8) by means of a pump (I). The temperature in the bottom phase of the column is set via a heat exchanger (J). The bottom phase (A) and the column (C), in particular, serve as the main reaction zone, the column C being able to be heated/cooled separately by means of a heat exchanger (K). In this case the temperature of the streams (7) and (8) is selected in such a manner that the heat of reaction can be removed with cooling water corresponding to the ambient temperature and the reaction between aldehyde and HCN in column part (C) is 80 to 99.9% complete.

The aldehyde may be fed separately or together with the catalyst ((2),(3)). Preferably, the aldehyde or the aldehyde/catalyst mixture (2)+(3) is mixed with a substream (6) from the absorption and condensation part (E) of the column which is taken off from an intermediate bottom phase (D). The catalyst may also be fed, e.g., via the pathway (4). In this case, the catalyst should, via the pathway (13), also arrive in part in the top circuit. The residual amounts of HCN present in stream (6) are reacted with the supplied aldehyde in the dwell time vessel (G), the (second) post-reaction zone, completely or virtually completely to the cyanohydrin. Thereafter, the stream is cooled to 0° C. to 25° C. in the heat exchanger (H) in order to ensure condensation/absorption of HCN which is as complete as possible. In particular, the intermediate bottom phase (D), the absorption and condensation part (E) and the dwell time vessel (G) serve as absorption and post-reaction zone. Owing to the amounts of cyanohydrin present in the stream (5), and the cooling which is performed, the residual gases exiting at the column top also contain only very low residual amounts of the aldehyde, and so no additional scrubbing for recovery of the aldehyde from the residual gas may be required. The cyanohydrin concentration may be set via corresponding metering from the column bottom phase (13), preferably in the range from 10% by weight to 70% by weight in stream (5). The purified gases are advantageously passed into a combustion unit. The product exiting with stream (9) has a molar ratio of hydrogen cyanide to unreacted aldehyde of greater than 1, which may contribute substantially to stabilizing the product. In addition, the product is clear and only slightly discolored, which underlines the extraordinarily high selectivity of this process procedure.

After passage through a post reactor (L), in which any residual fractions of the aldehyde present are reacted to completion to achieve equilibrium with hydrogen cyanide, the resulting product stream may be mixed with an acid. For this purpose, a suitable mixing element (M) may be used. The pH of the product (stream (11)) that is set in this case is between 1 and 4, preferably between 2 and 3.

Figure 1:
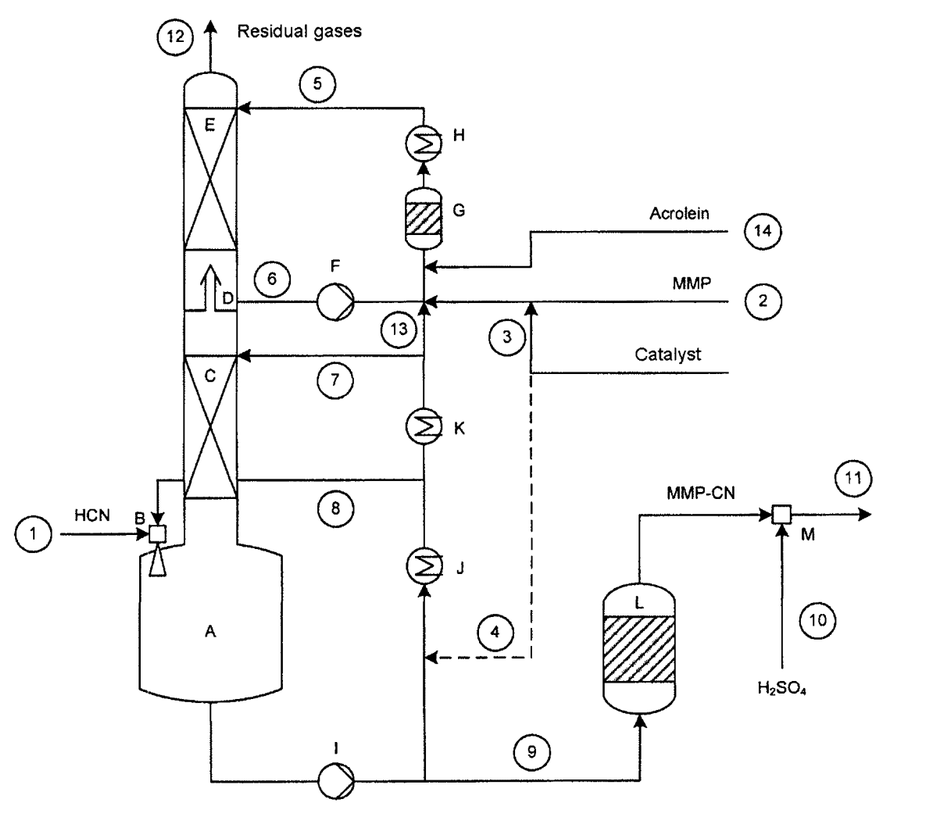
The FIGURE shows a process flow diagram according to one embodiment of the invention.

If the aldehyde is MMP, as shown in FIG. 1, the MMP starting material stream of the method described generally has a small content of methylmercaptan (MC), the predominant part of which would pass into the exhaust gas stream (12). This excess MC may also optionally be reacted with acrolein, which may be fed to the method, e.g. via stream (14), to form MMP and in succession with HCN to form MMP-CN and the yield thereby further increased.

In the method according to the invention, the catalyst used may be low-molecular-weight or heterogeneous amines or solutions of inorganic bases, or mixtures of acids and low-molecular-weight amines. These may also be needed in order to set the optimum pH range of approximately 4.5 to 6.0, preferably 5.0-5.5, that is required for the reaction (step a)), which may be measured using a pH electrode ("Aquatrode Plus with Pt 1000" type, manufacturer: Metrohm Schweiz AG) directly in the cyanohydrin having a typical water content of 2-14% by weight. The measurements are performed at a temperature of about 23° in a stirred vessel, the pH measurement being temperature-compensated. For following the reaction conditions close in time, and for elimination of measurement errors, pH measurements may be completed at one hour intervals, in each case the pH may be measured 4 times with determination of the mean value. Each measurement may take approximately 30 seconds. The measurement may, however, also be carried out directly during the reaction online in the reaction system at the temperature that is set there and converted to the pH at 23° C., which may further simplify the process control.

Low-molecular-weight amines, preferably having 1 to 36 carbon atoms, may have the particular advantage of virtually unlimited miscibility with the reaction medium, which in turn may favor a rapid reaction.

Low-molecular-weight amines which are preferred in this case are tri-($C_1$-$C_{12}$-alkyl)amines, preferably triethylamine or triisopropanolamine, dialkylaralkylamines, preferably dimethylbenzylamine, dialkylarylamines, preferably N,N-dimethylaniline, heterocyclic amines, preferably nicotinamide, imidazole, benzimidazole, 2-fluoropyridine, 4-dimethylaminopyridine, picoline or pyrazine.

Alternatively, heterogeneous amines of formula (I):

or polyvinylpyridine can also be used, wherein $R_1$ and $R_2$ are each independently, hydrogen, alkyl having chain lengths between $C_1$ and $C_{12}$, aryl or heteroaryl;

X is a number between 0 and 6, and

A is a natural or synthetic resin, preferably a polystyrene. These and the advantages associated therewith, such as, for instance, easier separability, low entrainment in subsequent reaction stages, are described in WO 2006/015684.

It may be preferred in this case that the catalyst according to formula I is a polymer-bound base selected from the group of the homologous dialkylaminoalkylpolystyrenes or dialkylaminomacroreticular resins.

It is particularly preferred that the catalyst according to formula I is diethylaminoethylpolystyrene, diethylaminomethylpolystyrene, dimethylaminomethylpolystyrene, diethylaminomethylmacroreticular resin or dimethylaminoethylpolystyrene.

The inorganic base may advantageously be alkali metal hydroxide, preferably NaOH or KOH, alkali metal cyanide, preferably NaCN or KCN, alkali metal carbonate, preferably $Na_2CO_3$ or $K_2CO_3$, or alkali metal hydrogencarbonate, preferably $NaHCO_3$ or $KHCO_3$, alone or in mixed form. These may have the advantage of particularly high catalytic activity which in turn favors a very rapid reaction and also the low potential interference of the low salt fractions resulting therefrom in the subsequent method. However, here, extremely good mixing and temperature control must be ensured, so that no significant byproduct formation proceeds.

As catalysts, advantageously, also mixtures of acids and the abovementioned low-molecular-weight amines may be used, in order to set the pH more readily in the desired range and to be able to stabilize it by the buffer action. Particularly advantageous in this case may be the use of organic acids such as short-chain fatty acids, e.g. acetic acid, formic acid, citric acid, and organic sulfonic acids, e.g. trifluoromethanesulfonic acid or the use of mineral acids such as, e.g., sulfuric acid or phosphoric acid, in combination with the low-molecular-weight amines.

According to a further preferred embodiment of the invention, the temperature in the main reaction zone may be selected in such a manner that the heat of reaction liberated can be given off to cooling water in accordance with the ambient temperature, which is a further great economic advantage of the method.

Correspondingly, the main reaction zone may be operated at a temperature of 20° C. to 80° C., preferably from 30° C. to 70° C., particularly preferably from 35° C. to 65° C. The reaction also proceeds comparatively rapidly in this range.

In the method according to the invention it is further preferred that the absorption and post-reaction zone is operated at a temperature of 0° C. to 30° C., preferably from 4° C. to 15° C. This may ensure a particularly efficient absorption of the hydrogen cyanide and still makes possible thorough reaction of HCN with the MMP to form MMP-cyanohydrin.

Furthermore, the use of a second post-reaction zone just upstream of the product discharge point for the MMP-cyanohydrin may be advantageous. This second post-reaction zone is operated at a similar temperature to the main reaction zone of 20° C. to 80° C., preferably 40° C. to 70° C., particularly preferably 45° C. to 65° C. In this manner a rapid and virtually quantitative completion of the reaction of HCN and MMP to form MMP-cyanohydrin shortly upstream of the product discharge may be ensured.

The method according to the invention may be advantageously operated at an absolute pressure of 0.9 to 5 bar, preferably 1.0 to 3 bar, particularly preferably 1 to 1.5 bar. This has the effect that rapid degassing of the absorbed HCN from the solution and corresponding losses may be thereby prevented.

The method according to the invention may employ a molar ratio of prussic acid to 3-(methylthio)propanal of 0.98 to 1.03, preferably 0.99 to 1.01. Firstly, losses of prussic acid may thus be avoided, which losses, especially on an industrial scale, would result in a great economic disadvantage. Secondly, unwanted prussic acid breakdown products such as, e.g., polymeric prussic acid or the saponification product formic acid which has corrosive properties against various metallic materials, may be avoided and corresponding disadvantageous effects to methionine in the downstream method stages may thereby be avoided.

In the method according to the invention, preferably, a weight ratio of catalyst to 3-(methylthio)propanal of 0.00005 to 0.002 may be used, particularly preferably 0.0001 to 0.001. This may simultaneously provide for a high reaction rate and a particularly low byproduct formation.

The method according to the invention may optionally be carried out batchwise, semicontinuously, or continuously, the continuous embodiment being particularly economical to operate on an industrial scale of greater than 10 000 tons/a.

The MMP-cyanohydrin produced according to the invention may have the following composition:

MMP-CN: 86-97% by weight,
MMP: 0-1% by weight,
HCN: 0.05-0.5% by weight,
$H_2O$: 2-14% by weight,
Oligomers: 0.01-0.1% by weight.

The molar yields based on MMP may be 99.50 to 99.99%.

The mixture containing a 2-hydroxy-4-(methylthio)butyronitrile according to the invention may, particularly advantageously, be used directly for producing methionine and 2-hydroxy-4-methylthiobutyric acid. For this purpose, it may either be aminated (aminonitrile pathway) or reacted with a mixture of ammonia and carbon dioxide (hydantoin pathway), in order to form methionine, or hydrolyzed directly to form 2-hydroxy-4-methylthiobutyric acid (methioninehydroxy analogs, MHA).

It has, furthermore, surprisingly been found that high-boiling MMP oligomers already present in MMP may for the most part be reacted in the method according to the invention to form the desired MMP-cyanohydrin. This is shown in that, e.g., the residue formed in the distillation of the products is markedly less after the reaction than before the reaction to form the MMP-cyanohydrin.

In particular, the use of the 2-hydroxy-4-(methylthio)butyronitrile-containing mixture according to the invention as a storage-stable form has proved advantageous. Storage stability in this context is taken to mean that on storage for at least 128 days at room temperature, that is to say at 20 to 25° C., only a loss of 2-hydroxy-4-methylthiobutyronitrile of less than 1% is analytically detectable. Suitable analytical methods are, in particular, the customary HPLC methods.

Having generally described this invention, a further understanding may be obtained by reference to certain specific examples which are provided hereinafter, for purposes of illustration only, and are not intended to be limiting unless otherwise specificed.

Analytical methods used:

The H2O content in MMP-CN was determined by the method of titration with biamperometric indication of the end point (Karl-Fischer titration).

For this purpose, 20-30 ml of titration medium (e.g. Hydranal Solvent 5, Fluka) were charged into the titration vessel and titrated to dryness using titration agent (e.g. Hydranal Titrant 5, Fluka). A sample quantity of approximately 500 mg was added to the initial charge that had been titrated to exhaustion (plastic disposable syringe) and titrated to the end point with titration agent. The exact sample weight was determined by differential weighing.

The procedure of this standard method is known to those skilled in the art (see, e.g., P. A. Bruttel, R. Schlink: Wasserbestimmung durch Karl-Fischer-Titration [Water determination by Karl-Fischer titration] Metrohm AG).

The free prussic acid content of the product was determined by the principle of ion chromatography (IC) using amperometric cyanide detection at an Ag working electrode, the sample preparation having proceeded by separating off the free prussic acid from the sample matrix by means of preparative column chromatography.

The preparative cyanide removal was performed, e.g., at room temperature, on a PRP-X 300 separation column, 250 mm length×4.1 mm internal diameter from Hamilton. The mobile phase consisted of a 5 mmolar sulfuric acid. At a flow rate of 1.0 ml/min, 100 μl of the sample solution (0.1 g of sample in 10 ml of mobile phase) were injected. The column eluate from 4 min to 8 min was collected in a 100 ml measuring flask, made up to the mark with ultrapure water and 100 μl were injected into the IC for cyanide determination.

Similarly to the sample solution, an NaCN calibration solution of known content was subjected to the preparative separation by means of column chromatography and 100 μl were injected into the IC for cyanide determination.

The ion-chromatographic cyanide determination was carried out at room temperature, e.g. on a Carbo F' ac PA1 separation column, 250 mm in length×4.0 mm internal diameter from Dionex. The mobile phase consisted of a solution of 1.5 g of sodium chloride and 1 ml of ethylenediamine in 1 l of a 50 mmolar sodium hydroxide solution. At a flow rate of 1.0 ml/min, 100 μl of sample solution or calibration solution were injected. The evaluation was performed by peak area comparison using the external standard method.

The procedure of this standard method is known to those skilled in the art.

The MMP-CN and MMP contents of the product were determined by means of isocratic ion exclusion chromatography on a cation exchanger with subsequent UV detection at 205 nm. The determination was carried out, e.g., on a PRP-X 300 separation column, 250 mm in length×4.1 mm internal diameter from Hamilton at a temperature of 25° C. The mobile phase consisted of a 5 mmolar sulfuric acid. At a flow rate of 1.0 ml/min, 100 μl of the respective sample solution (0.5 g of sample for MMP determination or 0.06 g of sample for MMP-CN determination in 50 ml of solvent) were injected. The calibration proceeded by injecting suitable calibration solutions (0.5 mg of MMP in 50 ml of solvent, or 50 mg of MMP-CN in 50 ml of solvent).

The solvent consisted of a mixture of 500 μl of 0.5 molar $H_2SO_4$ and 5 ml of acetonitrile which was diluted to 50 ml with ultrapure water.

The evaluation proceeded by peak area comparison by means of the external standard method.

The procedure of this standard method is known to those skilled in the art.

The components in the HCN-containing starting material gas nitrogen ($N_2$), carbon monoxide (CO), carbon dioxide ($CO_2$), methane ($CH_4$), ammonia ($NH_3$), prussic acid (HCN), water ($H_2O$), argon (Ar)/oxygen ($O_2$) (either/or), hydrogen ($H_2$) (only conditionally) and benzene as internal standard were determined by gas chromatography. The gas chromatograph 6890 (Agilent, based on the HP 6890) was used here. The gas chromatograph for this analysis was equipped with three separation columns: 1. HP-CPWAX 52CB 25 m*0.32 mm*0.2 μm (here NH3, HCN, water and benzene were separated), 2. molecular sieve 30 m*0.32 mm*12 μm (here $H_2$, $N_2$, $O_2$, CO and methane were separated) and 3. Plot Q 30 m*0.32 mm*20 μm (here $CO_2$ and benzene were separated), two thermal conductivity detectors (TCD), a pressure measuring unit and a mass flow meter (MFM) for helium. Column 1 was connected via a back injector to the back detector. Columns 2 and 3 were connected by a front injector to the front detector.

The procedure of this standard method is known to those skilled in the art.

The components methylmercaptan (MC) and methylmercaptopropionaldehyde (MMP) and acrolein (AC) of the residual gas exiting from the column top were determined by means of gas chromatography. In this case the gas chromatograph 7890A (Agilent) was used. The gas chromatograph was equipped for this analysis with a separation column (HP-INNOWAX 60 m*0.32 mm*0.25 μm) and a back detector (FID). The procedure of this standard method is known to those skilled in the art.

EXAMPLE 1

A setup as shown in FIG. 1 was used, having a column of 70 mm in diameter, which was equipped with 2 ordered packings (C) and (E) and which had heights in each case of 2500 and 1700 mm. Between the ordered packings were situated an intermediate bottom phase (D), from which a stream (6) can be taken off for operating a top circuit. Beneath the column was situated the column bottom phase having a volume of 4 liters. The diagram of this device is shown in the FIGURE.

With the stream (1), 8.98 kg/h of crude product gas from the production of hydrogen cyanide by the Andrussow method were fed via the gas blower (B) into the column bottom phase A which contained, based on weight: HCN: 8.87%, $H_2O$: 3.88%, $H_2$: 1.33%, $N_2$: 76.01%, $O_2$: 1.48%, CO: 5.67%, $CO_2$: 1.13%, $CH_4$: 0.39%. The incoming gas was mixed at the jet pump (B) with a circulating stream (8) of 300 kg/h. The temperature of the circulation stream was controlled here in such a manner that in the column bottom phase (A), at a filling state of 50%, a temperature of 50° C. prevailed. The feed stream (7) onto the ordered packing (C), at 40 kg/h, had a temperature of 35° C.

The methylthiopropionaldehyde was introduced into the reactor (G) via the feed (2) at a throughput of 2.966 kg/h. The reactor contained, based on weight: MMP: 96.46%, $H_2O$: 2.77%, MC: 0.2%. Via the feed line (3), at the same time 0.211 kg/h of a mixture of 99% by weight of MMP in the composition described above and 1% by weight of triethanolamine as catalyst were introduced into the reactor (G). The whole stream (5) consisting of the starting materials and the circulation stream (6) was supplied at 40 kg/h in the feed to the upper ordered packing (E) at a temperature of 6° C.

The molar starting material ratio HCN/MMP corresponded to 1. The product left the column bottom phase at 4.20 kg/h and had the following composition, based on weight:

MMP-CN: 90.43%, H$_2$O: 7.82%, MMP: 0.14%, HCN: 0.16%, MC: 0.01%. The exhaust gas left the column top at 8.07 kg/h and had the following composition based on weight: HCN: 0.00%, MMP: 0.07%, MC: 0.05%, H$_2$O: 1.34%, H$_2$: 1.48%, N$_2$: 86.02%, O$_2$: 1.64%, CO: 6.31%, CO$_2$: 1.26%, CH$_4$: 0.44%. The gases were fed to a combustion plant.

EXAMPLE 2

The setup of Example 1 was used.

With the stream (1), 8.94 kg/h of crude product gas of the production of hydrogen cyanide by the Andrussow method were fed via the gas blower (B) into the column bottom phase A which contained, based on weight: HCN: 8.9%, H$_2$O: 3.7%, H$_2$: 1.3%, N$_2$: 76.3%, O$_2$: 1.5%, CO: 5.6%, CO$_2$: 1.1%, CH$_4$: 0.4%. The incoming gas was mixed at the jet pump (B) with a circulating stream (8) of 280 kg/h. The temperature of the circulation stream was controlled in this case in such a manner that, in the column bottom phase (A), at a filling state of 50%, a temperature of 49.8° C. prevailed. The feed stream (7) onto the ordered packing (C) had a temperature of 35° C. at 40 kg/h.

The methylthiopropionaldehyde was introduced into the reactor (G) via the feed (2) at a throughput of 2.976 kg/h. It contained, based on weight: MMP: 96.9%, H$_2$O: 2.8%, MC: 0.2%. Via the feed line (3), at the same time, 0.2 kg/h of a mixture of 99% by weight of MMP in the above described composition and 1% by weight of triethanolamine as catalyst was introduced into the reactor (G). In addition, 2 kg/h of the bottom phase product were introduced via the pathway (13) into the reactor (G). The whole stream (5) consisted of the starting materials and the circulation stream (6) and the product stream (13) was 42 kg/h in the feed to the upper ordered packing (E) at a temperature of 5.5° C.

The molar starting material ratio HCN/MMP corresponded to 1. The product left the column bottom phase at 4.25 kg/h and had the following composition, based on weight:

MMP-CN: 90.06%, H$_2$O: 8.81%, MMP: 0.75%, HCN: 0.21%, MC: 0.01%. The exhaust gas left the column top at 7.88 kg/h and had the following composition based on weight: HCN: 0.00%, MMP: 0.09%, MC: 0.10%, H$_2$O: 0.6%, H$_2$: 1.50%, N$_2$: 86.60%, O$_2$: 1.70%, CO: 6.40%, CO$_2$: 1.20%, CH$_4$: 0.50%. The gases were fed to a combustion plant.

EXAMPLE 3

The setup of Example 1 was used.

With the stream (1), 8.94 kg/h of crude product gas of the production of hydrogen cyanide by the Andrussow method was fed via the gas blower (B) into the column bottom phase A which contained, based on weight: HCN: 8.9%, H$_2$O: 3.7%, H$_2$: 1.3%, N$_2$: 76.3%, O$_2$: 1.5%, CO: 5.6%, CO$_2$: 1.1%, CH$_4$: 0.4%. The incoming gas was mixed at the jet pump (B) with a circulating stream (8) of 280 kg/h. The temperature of the circulation stream was controlled in this case in such a manner that, in the column bottom phase (A), at a filling state of 50%, it had a temperature of 52° C. The feed stream (7) onto the ordered packing (C), at 40 kg/h, had a temperature of 35° C.

The methylthiopropionaldehyde was introduced into the reactor (G) via the feed (2) at a throughput of 2.976 kg/h. The reactor contained, based on weight: MMP: 96.9%, H$_2$O: 2.8%, MC: 0.2%. Via the feed line (3), at the same time, 0.2 kg/h of a mixture of 99% by weight of MMP in the above described composition and 1% by weight of triethanolamine as catalyst was introduced into the reactor (G). In addition, 2 kg/h of the bottom-phase product were introduced into the reactor (G) via the pathway (13). The whole stream (5) consisting of the starting materials and the circulation stream (6) and the product stream (13) was 42 kg/h at a temperature of 5.5° C. in the feed to the upper ordered packing (E).

The molar starting material ratio HCN/MMP corresponded to 1. The product left the column bottom phase at 4.25 kg/h and had the following composition based on weight: MMP-CN: 90.46%, H$_2$O: 8.81%, MMP: 0.35%, HCN: 0.18%, MC: 0.00%. The exhaust gas left the column top at 7.88 kg/h and had the following composition based on weight: HCN: 0.00%, MMP: 0.09%, MC: 0.10%, H$_2$O: 0.6%, H$_2$: 1.50%, N$_2$: 86.60%, O$_2$: 1.70%, CO: 6.40%, CO$_2$: 1.20%, CH$_4$: 0.50%. The gases were fed to a combustion plant.

From the product thus obtained, for determining the storage stability in further dependence on the water content and the pH, further samples listed in Table 1 were produced by corresponding addition of water and sulfuric acid and stored at 20° C. for up to 128 days.

The samples having a water content of 18.26 and 18.35% by weight, respectively (Examples 3b and 3d) do not correspond to the product according to the invention, but serve as comparison.

TABLE 1

Product of Example 3 with further variation of pH and water content (% by weight).

|  | pH | Water content | HCN content |
|---|---|---|---|
| Example 3a | 2 | 8.73 | 0.18 |
| Example 3b | 2 | 18.26 | 0.16 |
| Example 3c | 4 | 8.78 | 0.18 |
| Example 3d | 4 | 18.35 | 0.16 |

EXAMPLE 4

The setup of Example 1 was used, but without bottom-phase product feed (13) in the top product circuit.

With the stream (1), 8.95 kg/h of crude product gas of the production of hydrogen cyanide by the Andrussow method is fed via the gas blower (B) into the column bottom phase A which contains the following based on weight: HCN: 8.9%, H$_2$O: 3.9%, H$_2$: 1.3%, N$_2$: 76.2%, O$_2$: 1.4%, CO: 5.6%, CO$_2$: 1.1%, CH$_4$: 0.4%. The incoming gas was mixed at the jet pump (B) with a circulating stream (8) of 280 kg/h. The temperature of the circulation stream was controlled in this case in such a manner that, in the column bottom phase (A), at a filling state of 50%, it had a temperature of 65.0° C. The feed stream (7) onto the ordered packing (C), at 40 kg/h, had a temperature of 40° C.

The methylthiopropionaldehyde was introduced into the reactor (G) via the feed (2) at a throughput of 2.965 kg/h. The reactor contained, based on weight: MMP: 97.0%, H$_2$O: 1.9%, MC: 0.3%. Via the feed line (3), at the same time, 0.2 kg/h of a mixture of 99% by weight of MMP in the composition described above and 1% by weight of triethanolamine as catalyst were introduced into the reactor (G). The whole stream (5) consisting of the starting materials and the circulation stream (6), in the feed to the upper ordered packing (E), was 39 kg/h at a temperature of 5.9° C.

The molar starting material ratio HCN/MMP corresponded to 0.997. The product left the column bottom phase at 4.21 kg/h and had the following composition, based on weight: MMP-CN: 90.56%, H$_2$O: 7.56%, MMP: 0.16%, HCN: 0.04%. The exhaust gas left the column top at 8.04 kg/h and had the following composition, based on weight: HCN: 0.05%, MMP: 0.11%, MC: 0.09%, H$_2$O: 1.1%, H$_2$: 1.40%, N$_2$: 86.30%, O$_2$: 1.60%, CO: 6.20%, CO$_2$: 1.20%, CH$_4$: 0.40%. The gases were fed to a combustion plant.

From the product thus obtained, for determining the storage stability in further dependence on the water content and the pH, further samples listed in Table 2 were produced by appropriate addition of water and sulfuric acid and stored at 20° C. for up to 128 days.

The samples Examples 4b and 4d in Table 2 do not correspond to the product according to the invention, but serve as comparison.

TABLE 2

Product of Example 4 with further variation of pH and water content.

| | pH | Water content | HCN content |
|---|---|---|---|
| Example 4a | 2 | 7.49 | 0.04 |
| Example 4b | 2 | 17.23 | 0.04 |
| Example 4c | 4 | 7.53 | 0.04 |
| Example 4d | 4 | 17.32 | 0.04 |

During the storage experiments, over 128 days, the mass content (% by weight) of MMP-CN in the individual samples was determined by HPLC. The results are shown in Table 3.

TABLE 3

Mass fractions of MMP-CN in dependence on storage time, pH, water content and HCN content.

| Day | | Ex. 3a | Ex. 3b | Ex. 3c | Ex. 3d | Ex. 4a | Ex. 4b | Ex. 4c | Ex. 4d |
|---|---|---|---|---|---|---|---|---|---|
| | pH | 2 | 2 | 4 | 4 | 2 | 2 | 4 | 4 |
| | Water content | 8.73 | 18.26 | 8.78 | 18.35 | 7.49 | 17.23 | 7.53 | 17.32 |
| | HCN content | 0.18 | 0.16 | 0.18 | 0.16 | 0.04 | 0.04 | 0.04 | 0.04 |
| 1 | MMP- | 89.66 | 80.30 | 90.14 | 80.68 | 89.75 | 80.30 | 90.24 | 80.69 |
| 2 | CN | 89.64 | 80.29 | 90.14 | 80.67 | 89.75 | 80.28 | 90.22 | 80.69 |
| 4 | content | 89.67 | 80.28 | 90.12 | 80.65 | 89.73 | 80.24 | 90.22 | 80.58 |
| 8 | | 89.65 | 80.26 | 90.09 | 80.61 | 89.68 | 80.14 | 90.13 | 80.44 |
| 16 | | 89.64 | 80.23 | 90.08 | 80.52 | 89.67 | 80.05 | 90.13 | 80.25 |
| 32 | | 89.68 | 80.17 | 89.93 | 80.43 | 89.47 | 79.85 | 89.98 | 79.60 |
| 64 | | 89.67 | 79.96 | 89.86 | 79.94 | 89.22 | 79.42 | 89.48 | 78.76 |
| 128 | | 89.65 | 79.61 | 89.50 | 79.33 | 88.75 | 78.60 | 88.91 | 77.29 |

EXAMPLE 5

According to U.S. Pat. No. 4,960,932, MMP-CN was produced first from distilled MMP and distilled and subsequently condensed HCN in a stirred vessel that was adjusted to and maintained at 40° C., and stabilized by addition of 0.01 g of sulfuric acid (10%) per g of MMPCN. This MMP-CN was fine distilled by means of molecular distillation at 1 mbar and 90° C., all impurities except for water, and residues of MMP and HCN having been separated off. The product contained MMP-CN at 98% by weight and was cooled in a vessel to 0° C. From the resultant product, for determining the storage stability in further dependence on water content, on HCN content and on the pH, further samples listed in Table 2 were produced by addition of water and sulfuric acid and addition of distilled HCN and stored at 20° C. for up to 130 days.

The sample according to Example 5c in Table 4 does not correspond to the product according to the invention, but serves for comparison.

TABLE 4

Product from Example 5 with further variation of pH, HCN content and water content.

| | pH | Water content | HCN content |
|---|---|---|---|
| Example 5a | 2 | 6.62 | 0.19 |
| Example 5b | 4 | 6.51 | 0.19 |
| Example 5c | 4 | 18.12 | 0.01 |

During the storage experiments, the mass content (% by weight) of MMP-CN in the individual samples from Example 5 was determined over 130 days. The results are shown in Table 5.

TABLE 5

Mass fractions (% by weight) of MMP-CN in dependence on storage time, pH, water content and HCN content.

| Day | | Example 5a | Example 5b | Example 5c |
|---|---|---|---|---|
| | pH | 2 | 4 | 4 |
| | Water content | 6.62 | 6.51 | 18.12 |
| | HCN content | 0.19 | 0.19 | 0.01 |
| 1 | MMP-CN content | 91.45 | 91.80 | 80.98 |
| 4 | | 91.46 | 91.78 | 80.88 |
| 7 | | 91.43 | 91.76 | 80.67 |
| 14 | | 91.48 | 91.63 | 80.43 |

TABLE 5-continued

Mass fractions (% by weight) of MMP-CN in dependence on storage time, pH, water content and HCN content.

| Day | Example 5a | Example 5b | Example 5c |
|---|---|---|---|
| 21 | 91.45 | 91.62 | 79.72 |
| 35 | 91.48 | 91.47 | 78.78 |
| 56 | 91.43 | 91.43 | 77.96 |
| 130 | 91.44 | 91.07 | 77.70 |

The experimental results showed that the stability of the product was substantially affected by the HCN and water contents, as can be particularly advantageously set by the method described. The products having the highest HCN content according to Examples 3 and 5a and 5b generally showed the best stability. In addition, the products from Examples 3a, 3c, 5a and 5b were stabilized by the low water content. Setting the pH to a value of 2 likewise supported the stabilization of the product, the effect of acid addition or of pH, however, in comparison to the influencing factors HCN and water content, of subsidiary importance.

The invention claimed is:

1. A 2-hydroxy-4-methylthiobutyronitrile mixture, comprising:
   86 to 97% by weight of 2-hydroxy-4-methylthiobutyronitrile;
   2 to 14% by weight of water; and
   0.05 to 0.5% by weight of HCN;
   wherein
   a pH of the 2-hydroxy-4-methylthiobutyronitrile mixture is from 1 to 4, measured with a pH electrode at 23° C.

2. The 2-hydroxy-4-methylthiobutyronitrile mixture according to claim 1 wherein
   a loss of 2-hydroxy-4-methylthiobutyronitrile in the mixture on storage for 128 days is less than 1% by weight.

3. The 2-hydroxy-4-methylthiobutyronitrile mixture according to claim 2 wherein
   the loss of 2-hydroxy-4-methylthiobutyronitrile in the mixture on storage for 128 days is from 0.01 to 0.73% by weight.

4. The 2-hydroxy-4-methylthiobutyronitrile mixture according to claim 1 wherein
   the content of 2-hydroxy-4-methylthiobutyronitrile is 88 to 92% by weight, and
   the content of water is from 3 to 12% by weight.

5. The 2-hydroxy-4-methylthiobutyronitrile mixture according to claim 1 wherein
   the content of 2-hydroxy-4-methylthiobutyronitrile is 88 to 92% by weight, and
   the content of HCN is from 0.1 to 0.3% by weight.

6. The 2-hydroxy-4-methylthiobutyronitrile mixture according to claim 1 wherein
   the content of 2-hydroxy-4-methylthiobutyronitrile is 88 to 92% by weight, and
   the pH is from 2 to 3.

7. A method for producing the 2-hydroxy-4-(methylthio)butyronitrile mixture according to claim 1, comprising:
   a) reacting 3-methylmercaptopropionaldehyde with hydrogen cyanide in the presence of a base to form a reaction mixture comprising the 2-hydroxy-4-methylthiobutyronitrile;
   b) adjusting the water content of the reaction mixture to 2 to 14% by weight by water addition, optionally during the reaction, after the reaction or during and after the reaction;
   c) adjusting the HCN content of the reaction mixture to 0.05 to 0.5% by weight by HCN addition, optionally during the reaction, after the reaction or during and after the reaction; and thereafter
   d) adding acid to set the pH to 1-4.

8. The method according to claim 7, wherein the molar ratio of hydrogen cyanide to 3-methylmercaptopropionaldehyde is from 0.98 to 1.03.

9. The method according to claim 7, wherein in d) the pH is set to from 2 to 3.

10. The method according to claim 7, wherein in a),
    the reaction of 3-methylmercaptopropionaldehyde with hydrogen cyanide in the presence of a base is conducted in a main reaction zone of a reactor,
    residual amounts of gaseous hydrogen cyanide which leave the main reaction zone are absorbed in an absorption and post-reaction zone of the reactor, wherein the absorption and post-reaction zone comprises a mixture of 3-methylmercaptopropionaldehyde, catalyst, and optionally, 2-hydroxy-4-methylthiobutyronitrile and
    the residual hydrogen cyanide reacts with the 3-methylmercaptopropionaldehyde to form 2-hydroxy-4-methylthiobutyronitrile.

11. The method according to claim 10, wherein the mixture of 3-methylmercaptopropionaldehyde, catalyst, and optionally, 2-hydroxy-4-methylthiobutyronitrile in the absorption and post-reaction zone originates at least partially from the main reaction zone.

12. The method according to claim 10, wherein the main reaction zone comprises at least one of a stirred reactor, a loop reactor and a jet pump.

13. The method according to claim 10, wherein the absorption and post-reaction zone comprises at least one device for contacting a gas with a liquid, the device being selected from the group of devices consisting of a column, a tray column, a packed-bed column, a bubble-column reactor, a droplet column, a reactor having a mechanically agitated container, a submerged jet reactor and a jet pump.

14. The method according to claim 10, wherein the hydrogen cyanide is introduced into the main reaction zone as a product gas from a plant for producing hydrogen cyanide, the plant being connected to the reactor.

15. The method according to claim 14, wherein a hydrogen cyanide content of the product gas is 1 to 99% by weight.

16. The method according to claim 7, wherein the catalyst is selected from the group consisting of a low-molecular-weight amine, a heterogeneous amine, a solution of an inorganic base, and a mixture of an acid and low-molecular-weight amine.

17. The method according to claim 16, wherein the catalyst is a low-molecular-weight amine, which is selected from the group consisting of a tri-$(C_1$-$C_{12}$-alkyl)amine, a dialkylaralkylamine, a dialkylarylamine and a heterocyclic amine.

18. The method according to claim 16, wherein the catalyst is a mixture of an acid and low-molecular-weight amine, the acid being at least one selected from the group consisting of an organic acid, an organic sulfonic acid, and a mineral acid.

19. A method for producing the 2-hydroxy-4-(methylthio)butyronitrile mixture according to claim 1, comprising:
    a) preparing a mixture of 3-methylmercaptopropionaldehyde and a base having a water content of 2 to 14% by weight;
    b) adjusting the pH of the mixture to 4.5 to 6.0;
    c) adding HCN to the mixture having a pH of 4.5 to 6.0;
    d) reacting the 3-methylmercaptopropionaldehyde with the HCN in the presence of the base at a temperature of from 20 to 80° C. to form a reaction mixture comprising the 2-hydroxy-4-methylthiobutyronitrile;
    e) adjusting the HCN content of the reaction mixture to 0.05 to 0.5% by weight by HCN addition; and thereafter,
    f) adding acid to set the pH to 1-4,
    wherein pH adjustment is with a pH electrode at 23° C.,
    wherein a molar ratio of hydrogen cyanide to 3-methylmercaptopropionaldehyde in d) is from 0.98 to 1.03.

20. The method according to claim 19, wherein the molar ratio of hydrogen cyanide to 3-methylmercaptopropionaldehyde is from 0.99 to 1.01.

21. The method according to claim 19, wherein in d),
    the reaction of 3-methylmercaptopropionaldehyde with hydrogen cyanide in the presence of a base is conducted in a main reaction zone of a reactor,
    residual amounts of gaseous hydrogen cyanide which leave the main reaction zone are absorbed in an absorption and post-reaction zone of the reactor, wherein a temperature of the absorption and post-reaction zone is from 0 to 30° C., the absorption and post-reaction zone comprises a mixture of 3-methylmercaptopropionaldehyde, catalyst, and optionally, 2-hydroxy-4-methylthiobutyronitrile and at least a part of the residual hydrogen cyanide reacts with the 3-methylmercaptopropionaldehyde to form 2-hydroxy-4-methylthiobutyronitrile.

22. A method for producing D,L-methionine or 2-hydroxy-4-methylthiobutyric acid, comprising: employing the 2-hydroxy-4-(methylthio) butyronitrile mixture according to claim 1 as a starting material source or as an intermediate to prepare D,L-methionine or 2-hydroxy-4-methylthiobutyric acid.

* * * * *